(12) United States Patent
Mathey

(10) Patent No.: US 11,944,063 B2
(45) Date of Patent: *Apr. 2, 2024

(54) HYDRANGEA 'SMNHPH'

(71) Applicant: Spring Meadow Nursery, Inc., Grand Haven, MI (US)

(72) Inventor: Megan Mathey, Grand Haven, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/354,259

(22) Filed: Jun. 22, 2021

(65) Prior Publication Data

US 2022/0095563 A1 Mar. 31, 2022

Related U.S. Application Data

(63) Continuation of application No. 17/039,343, filed on Sep. 30, 2020, now Pat. No. Plant 33,207.

(51) Int. Cl.
*A01H 6/48* (2018.01)
*A01H 5/02* (2018.01)
*C12Q 1/6895* (2018.01)

(52) U.S. Cl.
CPC ............. *A01H 6/48* (2018.05); *A01H 5/02* (2013.01); *C12Q 1/6895* (2013.01); *C12Q 2600/13* (2013.01); *C12Q 2600/156* (2013.01)

(58) Field of Classification Search
CPC ........ A01H 6/48; A01H 5/02; C12Q 2600/13; C12Q 2600/156
USPC .......................................... 800/267
See application file for complete search history.

(56) References Cited

U.S. PATENT DOCUMENTS

| | | | |
|---|---|---|---|
| 5,034,323 A | 7/1991 | Jorgensen et al. | |
| 5,107,065 A | 4/1992 | Shewmaker et al. | |
| 5,453,566 A | 9/1995 | Shewmaker et al. | |
| 5,463,175 A | 10/1995 | Barry et al. | |
| 5,500,365 A | 3/1996 | Fischhoff et al. | |
| 5,633,435 A | 5/1997 | Barry et al. | |
| 5,689,052 A | 11/1997 | Brown et al. | |
| 5,759,829 A | 6/1998 | Shewmaker et al. | |
| 5,880,275 A | 3/1999 | Fischhoff et al. | |
| 6,423,885 B1 | 7/2002 | Waterhouse et al. | |
| 6,453,242 B1 | 9/2002 | Eisenberg et al. | |
| 6,528,700 B1 | 3/2003 | Baszczynski et al. | |
| 6,753,139 B1 | 6/2004 | Baulcombe et al. | |
| 6,785,613 B2 | 8/2004 | Eisenberg et al. | |
| 6,911,575 B1 | 6/2005 | Baszczynski et al. | |
| PP16,166 P2 | 12/2005 | Van Huylenbroeck | |
| PP16,812 P2 | 7/2006 | Bulk | |
| 7,138,565 B2 | 11/2006 | Waterhouse et al. | |
| 7,151,201 B2 | 12/2006 | Barbas, III et al. | |
| 7,177,766 B2 | 2/2007 | Eisenberg et al. | |
| PP18,438 P2 * | 1/2008 | Kolster .................. | A01H 6/48 Plt./250 |
| PP20,670 P3 | 1/2010 | Renault et al. | |
| 7,713,715 B2 | 5/2010 | Speer et al. | |
| 7,788,044 B2 | 8/2010 | Eisenberg et al. | |
| PP22,330 P2 | 12/2011 | Wood | |
| PP25,136 P2 | 12/2014 | Wood | |
| PP27,302 P2 | 10/2016 | Wood | |
| PP32,511 P2 | 11/2020 | Wood | |
| PP32,512 P2 | 11/2020 | Wood | |
| PP32,513 P2 | 11/2020 | Mathey | |
| PP33,207 P2 * | 6/2021 | Mathey .................. | Plt./250 |
| 2010/0076057 A1 | 3/2010 | Sontheimer et al. | |
| 2014/0179006 A1 | 6/2014 | Zhang | |
| 2014/0294773 A1 | 10/2014 | Brouns et al. | |

FOREIGN PATENT DOCUMENTS

| | | |
|---|---|---|
| WO | 99/31248 | 6/1999 |
| WO | 2014/068346 | 5/2014 |

OTHER PUBLICATIONS

CPVO Register Version 4.8.10 for Hydrangea Smnhph, retrieved on May 16, 23 at https://online.plantvarieties.eu/publicConsultationDetails?registerId=20220108&denomination=smnhph, 2 pp. (Year: 2023).*
Greer et al. In Vitro Germination and Dormancy Responses of Hydrangea macrophylla and Hydrangea paniculata Seeds to Ethyl Methane Sulfonate and Cold Treatment, HortScience 44(3):764-769, 2009 (Year: 2009).*
Kardos The Principles and Practices of Breeding Hydrangeas, Combined Proceedings International Plant Propagators' Society, vol. 56, 2006, 534-537. (Year: 2006).*
Liu et al. Shoot organogenesis in leaf explants of Hydrangea macrophylla 'Hyd1' and assessing genetic stability of regenerants using ISSR markers. Plant Cell Tiss Organ Cult (2011) 104: 111-117. (Year: 2011).*
Ruffoni et al. In Vitro Propagation of *Hydrangea* spp. Protocols for Micropropagation of Selected Economically-Important Horticultural Plants, Methods in Molecular Biology, vol. 994, 2013, Chap. 18, pp. 231-244. (Year: 2013).*
Beck, W. T. et al., Ploidy Levels and Interploid Hybridization in Panicle Hydrangea (*Hydrangea paniculata*), SNA Research Conference, vol. 59, 2014, pp. 181-187.
Allard, R.W., "Principles of Plant Breeding", Copyright 1960, Second printing Jun. 1964, pp. 477 pp. total.

(Continued)

*Primary Examiner* — June Hwu

(74) *Attorney, Agent, or Firm* — Warner Norcross + Judd LLP

(57) ABSTRACT

A hydrangea 'SMNHPH' having one or more of the following traits: 1) a compact habit, 2) panicle flowers that, when they age, transition from lime green to white to bright red pink, 3) exhibiting flowers at different age stages, such that an array of colors on the plant are exhibited at the same time 4) dense flower panicle, 5) thick, durable foliage, 6) strong stems, and 7) orange fall color.

16 Claims, 23 Drawing Sheets

(22 of 23 Drawing Sheet(s) Filed in Color)

(56) References Cited

OTHER PUBLICATIONS

Aukerman, M.J. et al., "Regulation of Flowering Time and Floral Organ Identity by a MicroRNA and Its APETALA2-Like Target Genes", The Plant Cell, vol. 15, Nov. 2003, pp. 2730-2741.
Barrangou, R. et al., "CRISPR Provides Acquired Resistance Against Viruses in Prokaryotes", Science, vol. 315, Mar. 23, 2007, pp. 1709-1712.
Baulcombe, D.C., "Fast forward genetics based on virus-induced gene silencing", Plant Biology, 1999 (2), pp. 109-113.
Becker, T.W. et el., "The cab-m7 gene: a light-inducible, mesophyll-specific gene of maize", Plant Molecular Biology 20, 1992, pp. 49-60.
Bragdø, M., "Interspecific Crosses in Lupinus; Cytology and Inheritance of Flower Colour", Institute of Genetics and Plant Breeding, Agricultural College of Norway, Vollebekk, Norway, Sep. 28, 1956, pp. 338-356.
Burton, R.A. et al., "Virus-Induced Silencing of a Plan Cellulose Synthase Gene", The Plant Cell, vol. 12, May 2000, pp. 691-705.
Charest, P.J. et al., "In vitro study of transgenic tobacco expressing *Arabidopsis* wild type and mutant acetohydroxyacid synthase genes", Plant Cell Reports, 1990 (8); pp. 643-646.
Creissen, G. et al., "Molecular characterization of glutathione reductase cDNAs from pea (*Pisum sativum* L.)", The Plant Journal, 1992 2(1), pp. 129-131.
De Block, M. et al., "Expression of foreign genes in regenerated plans and in their progeny", The EMBO Journal, vol. 3, No. 8, 1984, pp. 1681-1689.
Dihr, S.K. et al., "Regeneration of fertile plants from protoplasts of soybean (*Glycine max* L. Merr.): genotypic differences in culture response", Plant Cell Reports, 1992 (11) pp. 285-289.
Eichholtz, D.A. et al., "Expression of Mouse Dihydrofolate Reductase Gene Confers Methotrexate Resistance in Transgenic Petunia Plants", Somatic Cell and Molecular Genetics, vol. 13, No. 1, 1987, pp. 67-76.
Flavell, R.B., "Inactivation of gene expression in plants as a consequence of specific sequence duplication", Proc. Natl. Acad. Sci. USA, vol. 91, Apr. 1994, pp. 3490-3496.
Fontes, E.B.P. et al., "Characterization of an Immunoglobulin Binding Protein Homolog in the Maize floury-2 Endosperm Mutant", The Plant Cell, vol. 3, May 1991, pp. 483-496.
Gould, S.J. et al., "A Conserved Tripeptide Sorts Proteins to Peroxisomes", The Journal of Cell Biology, vol. 108, May 1989, pp. 1657-1664.
Haseloff, J. et al., "Simple RNA enzymes with new and highly specific endoribonuclease activities", Nature, vol. 334, Aug. 18, 1988, pp. 585-591.
Ishino, Y. et al., "Nucleotide Sequence of the iap Gene, Responsible for Alkaline Phosphatase Isozyme Conversion in *Escherichia coli*, and Identification of the Gene Product", Journal of Bacteriology, vol. 169,. No. 12, Dec. 1987, pp. 5429-5433.
Kalderon, D. et al., "A Short Amino Acid Sequence Able to Specify Nuclear Location", Cell, vol. 39, Dec. 1984 (part 2), pp. 499-509.
Knox, C.A. et al., "Structure and organization of two divergent a-amylase genes from barley", Plant Molecular Biology 9: 198, pp. 3-17, 1987.
Komatsuda, T. et al., "Genotype X Sucrose Interactions for Somatic Embryogenesis in Soybean", Cell Biology & Molecular Genetics, Mar. 1992, pp. 333-337.
Komatsuda, T. et al., "Maturation and germination of somatic embroys as affected by sucrose and plant growth regulators in soybeans Glycine gracilis Skvortz and *Glycine max* (L.) Merr.", Plant Cell, Tissue and Organ Culture 28, 1992, pp. 103-113.
Koncz, C. et al., "Expression and assembly of functional bacterial luciferase in plants", Proc. Natl. Acad. Sci. USA, vol. 84, Jan. 1987, pp. 131-135.
Lerner, D.R. et al., "Cloning and Characterization of Root-Specific Barley Lectin", Plant Physiol. 1989 (91), pp. 124-129.
Martinelli, F. et al., "Proposal of a Genome Editing System for Genetic Resistance to Tomato Spotted Wilt Virus", American Journal of Applied Sciences, 2014, 11 (11) pp. 1904-1913.
Montgomery, M.K. et al., "RNA as a target of double-stranged RNA-mediated genetic interference in Caenorhabditis elegans", Proc. Natl. Acad. Sci. USA, vol. 95, Dec. 1998, pp. 15502-15507.
Napoli, C. et al., "Introduction of a Chimeric Chalcone Synthase Gene into Petunia Results in Reversible Co-Suppression of Homologous Genes in trans", The Plant Cell, vol. 2, Apr. 1990, pp. 279-289.
Neuhaus, J-M et al., "A short C-terminal sequence is necessary and sufficient for the targeting of chitinases to the plant vacuole", Proc. Natl. Acad. Sci. USA, vol. 88, Nov. 1991, pp. 10362-10366.
Neuhuber, F. et al., "Susceptibility of transgene loci to homology-dependent gene silencing"Mol. Gen. Genet. 1994 (244) pp. 230-241.
Noman, A. et al., "CRISPR-Cas9: Tool for Qualitative and Quantitative Plant Genome Editing", Frontiers in Plant Science, vol. 7, Article 1740, Nov. 2016, pp. 1-17.
Pandey, P. et al., "Plant Regeneration from Leaf and Hypocotyl Explants of Glycine wightii (W. and A.) Verdc. varlongicauda", Japan. J. Breed. 1992 (42), pp. 1-5.
Perriman, R. et al., "A Ribozyme That Enhances Gene Suppression in Tobacco Protoplasts", Antisense Research and Development 1993 (3), pp. 253-263.
Sander, J.D. et al., "CRISPR-Cas systems for editing, regulating and targeting genomes", Nature Biotechnology, vol. 32, No. 4, Apr. 2014, pp. 347-356.
Shah, D.M. et al., "Engineering Herbicide Tolerance in Transgenic Plants", Science, vol. 233, Jul. 25, 1986, pp. 478-481.
Sharp, P.A., "RNAi and double-strand RNA", Genes & Development, 1999 (13), pp. 139-141, 4pp. total.
Sheehy, R.E. et al., "Reduction of polygalacturonase activity in tomato fruit by antisense RNA", Prox. Natl. Acad. Sci. USA, vol. 85, Dec. 1988, pp. 8805-8809.
Shetty, K. et al., Stimulation of in vitro shoot organogenesis in Glycine max (Merrill.) by allantoin and amides, Plant Science, 81, 1992, pp. 245-251.
Borek, R. et al., "CRISPR-Mediated Adaptive Immune Systems in Bacteria and Archaea", Annu. Rev. Biochem., 2013 (82), pp. 237-266.
Steinecke, P. et al., "Expression of a chimeric ribozyme gene results in endonucleolytic cleavage of target mRNA and a concomitant reduction of gene expression in vitro", The EMBO Journal, vol. 11, No. 4, 1992, pp. 1525-1530.
Stephens, P.A. et al., "Agronomic evaluation of tissue-culture-derived soybean plants", Theor. Appl. Genet., 1992 (82), pp. 633-635.
Stiefel, V. et al., "Expressionof a Maize Cell Wall Hydroxyproline-Rich Glycoprotein Gene in Early Leaf and Root Vascular Differentiation", The Plant Cell, vol. 2, Aug. 1990, pp. 785-793.
Teeri, T.H. et al., "Gene fusions to IacZ reveal new expression patterns of chimeric genes in transgenic plants", The EMBO Journal, vol. 8, No. 2, 1989, pp. 343-350.
Vainstein, A., "Breeding for Ornamentals: Classical and Molecular Approaches", Springer-Science+Business Media, B.V., 2002, 386 pp. total.
Wang, S. et al., "Efficient targeted mutagenesis in potato by the CRISPR/Cas9 system", Plant Cell Rep, 2015 (34);pp. 1473-1476.
Zamore, P.D. et al., "RNAi: Double-Stranded RNA Directs the ATP-Dependent Cleavage of mRNA at 21 to 23 Nucleotide Intervals", Cell, vol. 101, Mar. 31, 2000, pp. 25-33.
Zhang, B. et al., "Exploiting the CRISPR/Cas9 System for Targeted Genome Mutagenesis in Petunia", Scientific Reports, 2016, pp. 1-8.

* cited by examiner

Conventional Leaf   'SMNHPH' Leaf

Conventional Leaf      'SMNHPH' Leaf

'SMNHPH' Dense Flower Panicle

'DVP PINKY' PP16,166 Flower Panicle

'SMNHPH' Dense Flower Panicle

'SMNHPM' PP32,513 Flower Panicle

'SMNHPH' - Strong Stems    Conventional Hydrangea Paniculata - Weak Stems

'SMNHPH'  'RENHY' PP20,670

Strong Stems  Weak Stems

HYDRANGEA 'SMNHPH'

CROSS-REFERENCE TO RELATED APPLICATIONS

This application claims priority to U.S. patent application Ser. No. 17/039,343, filed Sep. 30, 2020, entitled *Hydrangea paniculata* 'SMNHPH' LITTLE LIME PUNCH—the disclosure of which is hereby incorporated by reference in its entirety.

FIELD OF INVENTION

The present disclosure relates to the field of hydrangea plants, and more particularly toward the field of ornamental hydrangea plants and methods of breeding the same.

BACKGROUND

The genus *Hydrangea paniculata* belongs to the plant family Hydrangeaceae and is divided into 70-75 different species, which are endemic to Asia and North and South America. Although *Hydrangea paniculata* is native to Japan, Taiwan, and parts of China, it is grown in landscapes around the world (3, 9). Breeding efforts have recently been directed towards smaller stature, quality architecture, panicle size, and coverage of sterile (showy) florets, among other attributes. In nature, *H. paniculata* occurs as diploid, tetraploid, and hexaploid cytotypes, where 1x=18. There is evidence that most plants in cultivation are tetraploids.

In conventional *Hydrangea paniculata* breeding, there has been interest in the development of new forms, brighter aging flower color and earlier flowering plants. The conventional *Hydrangea paniculata* varieties today cover a range of different habits, lace-cap and mop head panicles, and panicle color.

*Hydrangea paniculata* can be propagated from seed, cuttings, and tissue culture. Germination, and propagation via cutting can be used as well.

SUMMARY

The cultivar 'SMNHPH' has not been observed under all possible environmental conditions. The phenotype may vary somewhat with variations in environment such as temperature, day length, and light intensity, without, however, any variance in genotype.

In one embodiment, the following traits have been repeatedly observed and are determined to be the unique characteristics of 'SMNHPH'. These characteristics in combination distinguish 'SMNHPH' as a new and distinct *Hydrangea* cultivar:

1. Compact plant habit.
2. Flowers age attractively to a rich, deep pink.
3. Exhibits flowers at different age stages throughout transition stages
4. Dense panicle.
5. Thick, durable foliage.
6. Strong stems.
7. Orange fall color.

In one embodiment, a hydrangea plant variety may include one or more of the physiological and morphological characteristics of the hydrangea plant of variety 'SMNHPH'. For instance, the hydrangea plant variety may include one or more of the seven characteristics listed above. In one embodiment, a hydrangea plant variety may include one or more of the following: orange fall color, a dense panicle, and flowers that age attractively to a rich, deep pink.

In one embodiment, a method of producing F1 seed or embryo may involve providing a hydrangea plant variety having one or more of the physiological and morphological characteristics of the hydrangea plant of variety 'SMNHPH', including one or more of the following: compact plant habit, flowers that age attractively to a rich, deep pink, exhibiting flowers at different age stages throughout transition stages, a dense panicle, thick, durable foliage, strong stems, and orange fall color.

In one embodiment, a tissue or cell culture of regenerable cells produced from a hydrangea plant of variety 'SMNHPH' is provided.

The foregoing and other embodiments can each optionally include one or more of the following features, alone or in combination. In particular, one embodiment includes all the following features in combination.

The tissue or cell culture may include tissues or cells from a plant part that include at least one of leaves, pollen, embryos, cotyledons, ovules, protoplasts, callus, pollen, seeds, petiole, hypocotyl, meristematic cells, roots, root tips, pistils, anthers, flowers, and stems.

A hydrangea plant regenerated from the tissue or cell culture may be provided.

In one embodiment, a method of developing a hydrangea plant variety having the physiological and morphological characteristics of a hydrangea plant of variety 'SMNHPH' may be provided. The method may include genotyping a hydrangea plant of variety 'SMNHPH', wherein the genotyping includes obtaining a sample of nucleic acids from the plant and detecting in the nucleic acids a plurality of polymorphisms, and using the identified polymorphisms for marker-assisted selection in a breeding program.

In one embodiment, a method for developing a hydrangea plant variety may be provided. The method may include one or more of the following steps: a) identifying and selecting a spontaneous mutation of a hydrangea plant of variety 'SMNHPH' or a part thereof, and cultivating the selected spontaneous mutation plant or plant part; b) introducing a mutation into the genome of a plant of variety 'SMNHPH' or a part thereof, and cultivating the mutated plant or plant part; and c) transforming a hydrangea plant of variety 'SMNHPH' with a transgene.

The foregoing and other embodiments can each optionally include one or more of the following features, alone or in combination. In particular, one embodiment includes all the following features in combination.

A hydrangea plant may be produced by cultivating the selected spontaneous mutation plant or plant part.

A hydrangea plant may be produced by cultivating the mutated plant or plant part.

The mutation may be introduced using a method comprising one or more of the following: temperature, long-term seed storage, tissue culture conditions, ionizing radiation, chemical mutagens, targeting induced local lesions in genomes, zinc finger nuclease mediated mutagenesis, CRISPR/Cas9, meganucleases, and gene editing.

The method may include the transgene conferring resistance to a herbicide, insecticide, or disease. A herbicide, insecticide, or disease resistant plant may be produced by the method, which includes a transgene conferring resistance.

In one embodiment, a method of producing an F1 seed or embryo may be provided, where the method includes crossing a hydrangea plant of variety 'SMNHPH' with a second plant and harvesting the resultant F1 seed or embryo.

The foregoing and other embodiments can each optionally include one or more of the following features, alone or in combination. In particular, one embodiment includes all the following features in combination.

The method of producing an F1 seed or embryo may include the second plant being another plant of variety 'SMNHPH'.

The method of producing an F1 seed or embryo may include the second plant being a plant of a different variety from the variety 'SMNHPH'.

The method of producing an F1 seed or embryo may include producing a *hydrangea plant by cultivating the harvested F1 seed or embryo*.

In one embodiment, a method of producing an F1 seed or embryo may include providing a hydrangea plant having one or more physiological and morphological characteristics of a hydrangea plant of variety 'SMNHPH'. The method may include crossing the hydrangea plant with a second plant and harvesting the resultant F1 seed or embryo, where the one or more physiological and morphological characteristics of the hydrangea plant include at least one of orange fall color, a flower panicle density score greater than 85, and flowers that age to a rich, deep pink.

The foregoing and other embodiments can each optionally include one or more of the following features, alone or in combination. In particular, one embodiment includes all the following features in combination.

The hydrangea plant may be produced by cultivating the harvested F1 seed or embryo yielded according to the method of producing an F1 seed or embryo.

The one or more physiological and morphological characteristics of the hydrangea plant include a flower panicle density that is greater than 90. The flower panicle density may be about 137 in one aspect of the hydrangea plant.

In one embodiment, a hydrangea plant variety may be provided having one or more physiological and morphological characteristics of a hydrangea plant of variety 'SMNHPH', where the one or more physiological and morphological characteristics of the hydrangea plant include at least one of orange fall color, a flower panicle density score greater than 85, and flowers that age to a rich, deep pink.

The one or more physiological and morphological characteristics of the hydrangea plan may include a flower panicle density that is greater than 90.

Before the embodiments of the invention are explained in detail, it is to be understood that the invention is not limited to the details of operation or to the details of construction and the arrangement of the components set forth in the following description or illustrated in the drawings. The invention may be implemented in various other embodiments and of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the invention to any specific order or number of components. Nor should the use of enumeration be construed as excluding from the scope of the invention any additional steps or components that might be combined with or into the enumerated steps or components. Any reference to claim elements as "at least one of X, Y and Z" is meant to include any one of X, Y or Z individually, and any combination of X, Y and Z, for example, X, Y, Z; X, Y; X, Z; and Y, Z.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

'SMNHPH' is illustrated by the accompanying photographs which show the plant's form, foliage, and inflorescences. The patent or patent application contains photographs executed in color. The colors shown are as true as can be reasonably obtained by conventional photographic procedures. Colors in the photographs may differ slightly from the color values cited in the detailed botanical description, which accurately describe the colors of the new hybrid *Hydrangea*. Age of the plants photographed is between 2 to 3 years. All plants were container grown in Grand Haven, Michigan and photographed during 2020.

DEFINITIONS

In the description and tables herein, a number of terms are used. In order to provide a clear and consistent understanding of the specification and claims, including the scope to be given such terms, the following definitions are provided:

Allele. "Allele" is any of one or more alternative forms for a gene.

Border Pattern. A "border pattern" refers to a pattern expressed on the flower where the color along the outer margin of the flower is different from the color of the rest of the flower. The color of the border along the outer margin of the flower may be thick or thin and solid or semi-solid. The color of the border along the outer margin and the rest of the flower may also vary in all colors and border patterns. Color, as referred to here, includes all pigmented colors and shades in-between, white, and unpigmented.

Gene. As used herein, "gene" refers to a segment of nucleic acid.

Locus. A "locus" is the position or location of a gene on a chromosome.

Plant Parts. A "plant part" or "a part thereof" is meant to refer to any part of the plant and includes but is not limited to, regenerable cells which may include plant calli, plant clumps, plant protoplast, plant cells, embryos, protoplasts, meristematic cells, callus, pollen, leaves, ovules, anthers, cotyledons, hypocotyl, pistils, roots, root tips, fruit, flowers, seeds, shoot, petiole, or stems.

Progeny. As used herein, the descendants of one or more of the parental lines and includes an $F_1$ *Hydrangea paniculata* plant produced from the cross of two *Hydrangea paniculata* plants where at least one plant includes a *Hydrangea paniculata* plant disclosed herein and progeny further includes, but is not limited to, subsequent $F_2$, $F_3$, $F_4$, $F_5$, $F_6$, $F_7$, $F_8$, $F_9$, and $F_{10}$ generational crosses with the recurrent parental line.

DETAILED DESCRIPTION

All publications cited in this application are herein incorporated by reference in their entirety. The present disclosure relates to the field of ornamental *Hydrangea paniculata* plants and plant breeding. The disclosure provides new, distinct and stable *Hydrangea paniculata* plants with compact habit, panicle flowers that, with age, transition from lime green to white to bright pink and have multi-age flowers on the same plant in different periods of transition. This combination of traits has not been observed in any known *Hydrangea paniculata*, but was discovered through the Applicant's breeding program.

*Hydrangea paniculata* is considered a valuable ornamental plant. Thus, continuing efforts of ornamental plant breeders are directed to developing plants with novel characteristics, such as strong stems, early flowering, vibrant flower color, and growth habit. To accomplish this goal, the breeder may select and develop plants that have traits that result in superior *Hydrangea paniculata* varieties.

Figure 1:
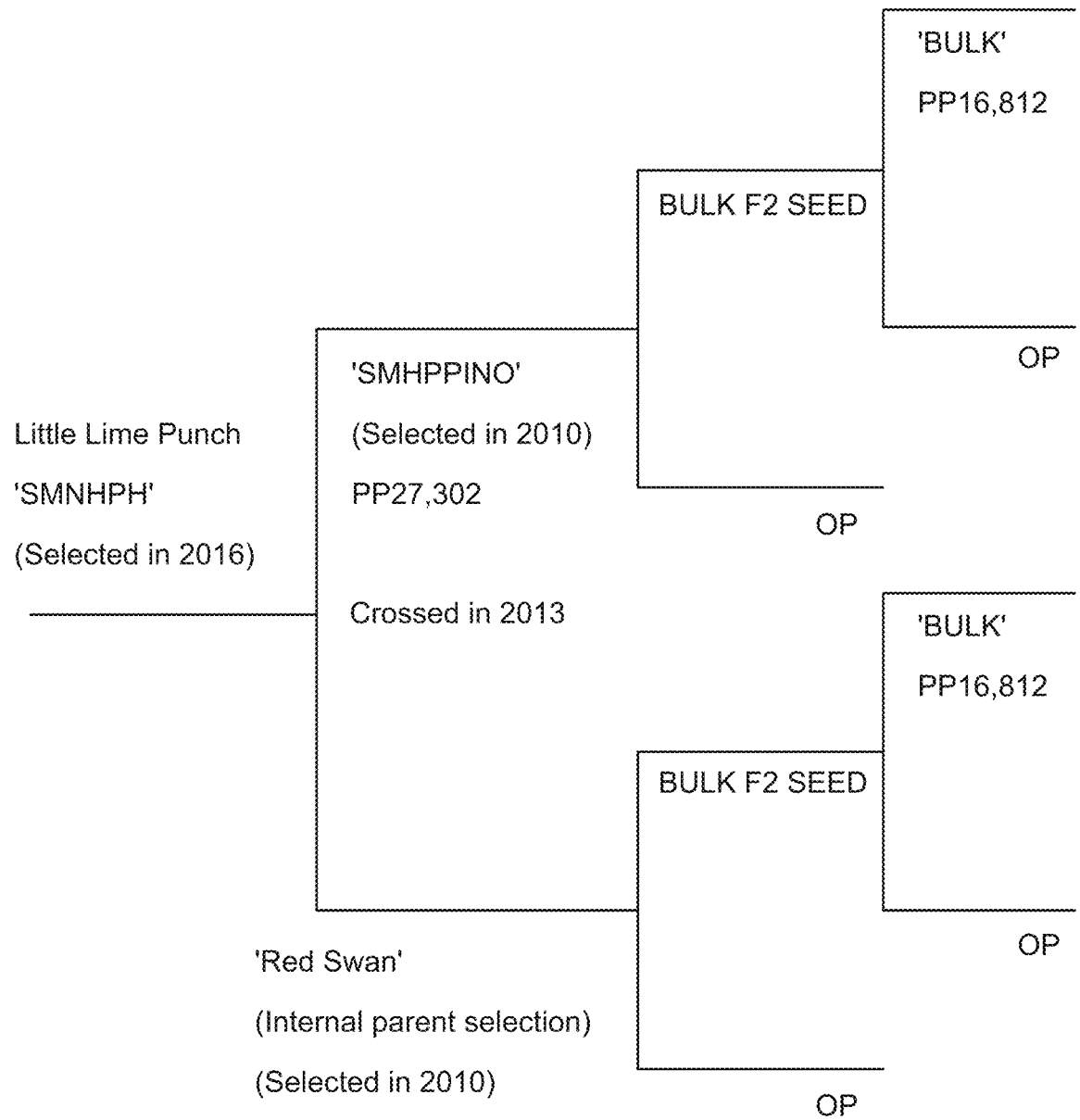
FIG. 1 shows the pedigree of *Hydrangea paniculata* 'SMNHPH'.

*Hydrangea paniculata* 'SMNHPH' was created by recurrent crossing and selection and is the result of three generations of controlled crossing, and is a hybrid varietal resulting from the crossing of a first varietal and a second varietal by artificial pollination. The first varietal and the second varietal had been previously bred for target characteristics. The first varietal is a female parent (i.e., the seed parent) and is the 'SMNHPPINO' variety (U.S. Plant Pat. No. 27,302), which originated from an F2 generation of seed from the 'BULK' variety (U.S. Plant Pat. No. 16,812) via open pollination and selection for target properties. The second varietal is the male parent (i.e., the pollen parent) and is an unpatented, Applicant-developed *Hydrangea paniculata* designated by Applicant as the 'RED SWAN' variety, which originated from an F2 generation of seed from the 'BULK' variety (U.S. Plant Pat. 16,812) via open pollination and selection for target properties. The pedigree for the *Hydrangea paniculata* 'SMNHPH' can be summarized by the lineage depicted in FIG. 1.

The seeds resulting from pollination of the 'SMNHPPINO' variety and the 'RED SWAN' variety were sown and plants were obtained which were physically and biologically different from each other. Selective study resulted in the identification of a single F1 plant, to yield the *Hydrangea paniculata* 'SMNHPH'. The resulting plants and the 'SMNHPH' plant were cultivated internally and have not been sold or offered for sale more than a year prior to the earliest effective filing date of this application.

It has been found that the 'SMNHPH' variety described in the present application possesses the following characteristics:
1. compact plant habit,
2. flowers age attractively to a rich, deep pink,
3. exhibits flowers at different age stages throughout transition stages,
4. dense flower panicle,
5. thick, durable foliage,
6. strong stems, and
7. orange fall color.

The 'SMNHPH' variety meets the needs of the horticultural industry. It can be grown to advantage as ornamentation in parks, gardens, public areas, and in residential settings. Accordingly, the 'SMNHPH' plant is particularly well suited for growing in the landscape.

The 'SMNHPH' variety of the present application can readily be distinguished from its ancestors. More specifically, the 'SMNHPPINO' variety (i.e., the seed parent) exhibits flowers with pale pink color in the Fall, whereas the 'SMNHPH' variety exhibits flowers which turn a richer red-pink in the Fall. Additionally, the 'SMNHPH' variety has thicker, darker green foliage than the 'SMNHPPINO' variety.

The 'RED SWAN' variety (i.e., the pollen parent) exhibits flowers that turn pink earlier compared to the flowers of the 'SMNHPH' variety, which stay white longer before turning a rich red-pink. The 'SMNHPH' variety also has larger, more dense flowers than the 'RED SWAN' variety.

The 'BULK' variety (i.e., the "grandparent" of both the seed and pollen parent) exhibits less dense open flower panicles, larger more open habit and less vibrant flower age, whereas the 'SMNHPH' variety exhibits densely packed flower panicles, tighter internodes, and more rich flower age.

Plants of the cultivar 'SMNHPH' can be compared to the variety *Hydrangea paniculata* 'Jane', USPP 22,330. These varieties are similar in several horticultural characteristics; however, 'SMNHPH' differs in one or more of the following:
1. The 'SMNHPH' variety has larger inflorescences than this comparator.
2. Flowers of the 'SMNHPH' variety hold their color longer than this comparator.
3. Stems of the 'SMNHPH' variety are stronger than stems of 'Jane'.

The 'SMNHPH' variety has been found to undergo asexual propagation at a commercial greenhouse in Grand Haven, Michigan. Subsequent asexual propagation has shown that the features of this cultivar are stable and reproduced true to type in four successive generations.

As noted above, the 'SMNHPH' variety has several characteristics that differ from its ancestors. The 'SMNHPH' variety provides a compact habit, and panicle flowers that, when they age, transition from lime green to white to bright red pink. The 'SMNHPH' variety exhibits flowers at different age stages, such that an array of colors on the plant are exhibited at the same time.

The 'SMNHPH' variety or the breeding methods described herein with respect to the 'SMNHPH' variety, or both, provide a *Hydrangea paniculata* having one or more characteristics not present in its ancestors.

One embodiment of the 'SMNHPH' variety or a *Hydrangea paniculata* bred according to the breeding methods described herein, or both, is a compact plant habit. Compact plant habit is defined by internode length for *Hydrangea paniculata*, and a plant is considered to be of compact nature if average internode length when grown in a container for commercial sale is 6 cm or less. Plants exhibiting non-compact habits have an average internode length greater than 6 cm and up to but not limited to 8 cm. The 'SMNHPH' variety may have an average internode length of between 5 and 6 cm.

Another embodiment of the 'SMNHPH' variety or a *Hydrangea paniculata* bred according to the breeding methods described herein, or both, is flowers that age attractively to a rich, deep pink.

Figure 2:
FIG. 2 shows plants of 'SMNHPH' grown outdoors in Grand Haven, MI during early Fall (second week of September). Plants have both white and pink flowers.
Figure 3:
FIG. 3 shows an alternative view of the 'SMNHPH' of FIG. 2.
Figure 4:
FIG. 4 shows the inflorescence color of the plants in FIG. 1 approximately 10 days earlier, before the rich pink color forms.
Figure 5:
FIG. 5 shows an enlarged view of the plants in FIG. 4.
Figure 6:
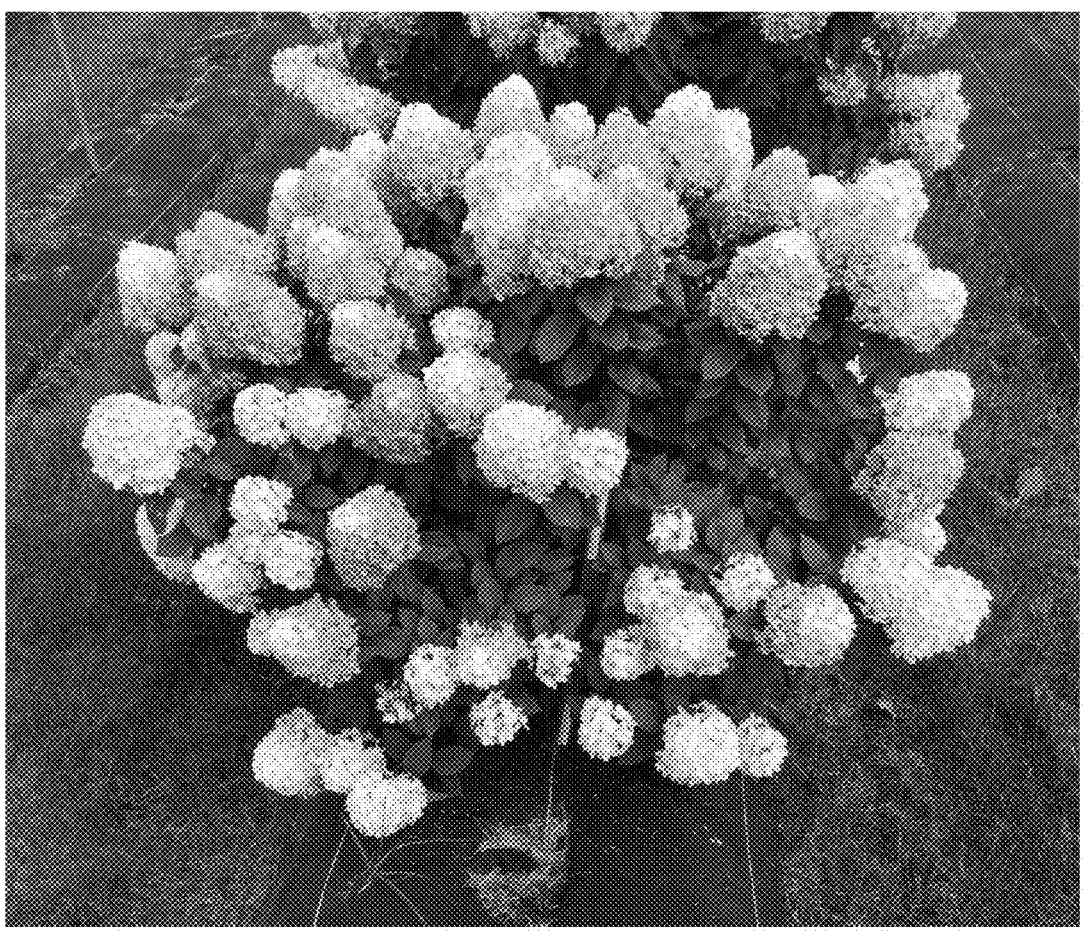
FIG. 6 shows an alternative view of the plants in FIG. 4.
Figure 7:
FIG. 7 shows yet another view of the plants in FIG. 4.
Figure 8:
FIG. 8 shows compact habit and plant after all flowers have fully transitioned.
Figure 9:
FIG. 9 shows an alternative view of the plants in FIG. 8.
Figure 10:
FIG. 10 shows the late Summer (late August) color of a maturing inflorescence, just beginning to change color of a container-grown plant.
Figure 11:
FIG. 11 shows the early Summer (mid-July) color of a mature inflorescence color of a container-grown plant.
Figure 12:
FIG. 12 shows an alternative view of FIG. 11.
Figure 13:
FIG. 13 shows an alternative view of FIG. 11.
Figure 14:
FIG. 14 shows orange fall color of the 'SMNHPH' variety.
Figure 15:
FIG. 15 shows progression of fall color of the 'SMNHPH' variety from greyed-red to orange-red in one embodiment according to the present disclosure.
Figure 16:
FIG. 16 shows fall color in one embodiment according to the present disclosure.
Figure 17:
FIG. 17 shows fall color in one embodiment according to the present disclosure.

Another embodiment of the 'SMNHPH' variety or a *Hydrangea paniculata* bred according to the breeding methods described herein, or both, is exhibits flowers at different age stages throughout transition stages. A conventional *Hydrangea paniculata* has the same age flowers that open and begin their color transition at the same time making a uniform non-contrasting color shift. 'SMNHP' may have all flowers formed and spaced generally uniformly on the plant; however, the flowers may be at different ages making a stark contrast when a newly maturing flower is white at the same time that a more mature flower has already progressed to its final bright red pink stage. This behavior can be seen in FIGS. 2 and 3.

Figure 20:
FIG. 20 shows flower panicle density of the 'SMNHPH' variety relative to flower panicle density of the 'DVP PINKY' *Hydrangea paniculata* (PP16,166).
Figure 21:
FIG. 21 shows flower panicle density of the 'SMNHPH' variety relative to flower panicle density of the 'SMNHPM' variety *Hydrangea paniculata* (PP32,513).

Another embodiment of the 'SMNHPH' variety or a *Hydrangea paniculata* bred according to the breeding methods described herein, or both, is dense flower panicles. Panicle density may be defined as a ratio of total (sterile and fertile) flower number divided by the length of panicle. For the 'SMNHPH' variety at the early flower maturation (week 1 or 2 post opening) stage of development, average fertile flower count per panicle may be approximately 620 and average sterile florets per panicle may be approximately 238. Total flower number per panicle on the 'SMNHPH' variety may be approximately 858 and average length may be 6.29" for an average density score of 136.41 (flowers per panicle length), which is greater than a density score of 85 and also greater than a density score of 100, in contrast to conventional *Hydrangea paniculata*. In one embodiment, the total flower number for the 'SMNHPH' variety may be greater than a conventional *Hydrangea paniculata*, facilitating a greater density score. Additionally, density of the 'SMNHPH' variety may be greater than conventional *Hydrangea paniculata* at least in part because the flower panicle length of the 'SMNHPH' variety is shorter than conventional *hydrangea paniculata* for a given number of panicle flowers. In other words, the greater the density score, the greater the density of flower panicles. A conventional *Hydrangea paniculata*, such as the 'DVP PINKY' (PP16,166), may have a density score of about 73 with a total average number of flowers per panicle being about 766 (557 fertile flowers per head and 209 sterile flowers per head) and an average length of about 10.5". With a density score of 85 or greater, 90 or greater, 100 or greater, or 130 or greater, the 'SMNHPH' variety has greater density flower panicles. Comparing the panicle flower density of the 'SMNHPM' variety yields similar results—the 'SMNHPM' variety (PP32,513) has a density score of about 81, with 424 flowers (102 fertile flowers per head and 322 sterile flowers per head) and a panicle length of 5.24". Accordingly, the 'SMNHPH' variety has a density of flower panicles that is greater than conventional *Hydrangea paniculata*. This increase in density of flower panicles can be seen in FIGS. 20 and 21, which show density of flower panicles of 'SMNHPH' relative to flower panicles of two conventional *Hydrangea paniculata*—the 'DVP PINKY' variety and the 'SMNHPM' variety. Panicle width may also affect density of flower panicles—but this property is represented within the density score.

The density scores identified herein with respect to the 'SMNHPH' variety and conventional *Hydrangea paniculata* are measurable at the early flower maturation (week 1 or 2 post opening) stage of development (measurements taken on the same age plants and flowers). It is noted that the physical density may change as the flower matures, sepals fully open, and the panicle continues to grow in length. However, with reference to the late stage or full maturation stage of development, the density score of the 'SMNHPH' variety is significantly greater than conventional varieties of *Hydrangea paniculata*.

Figure 18:
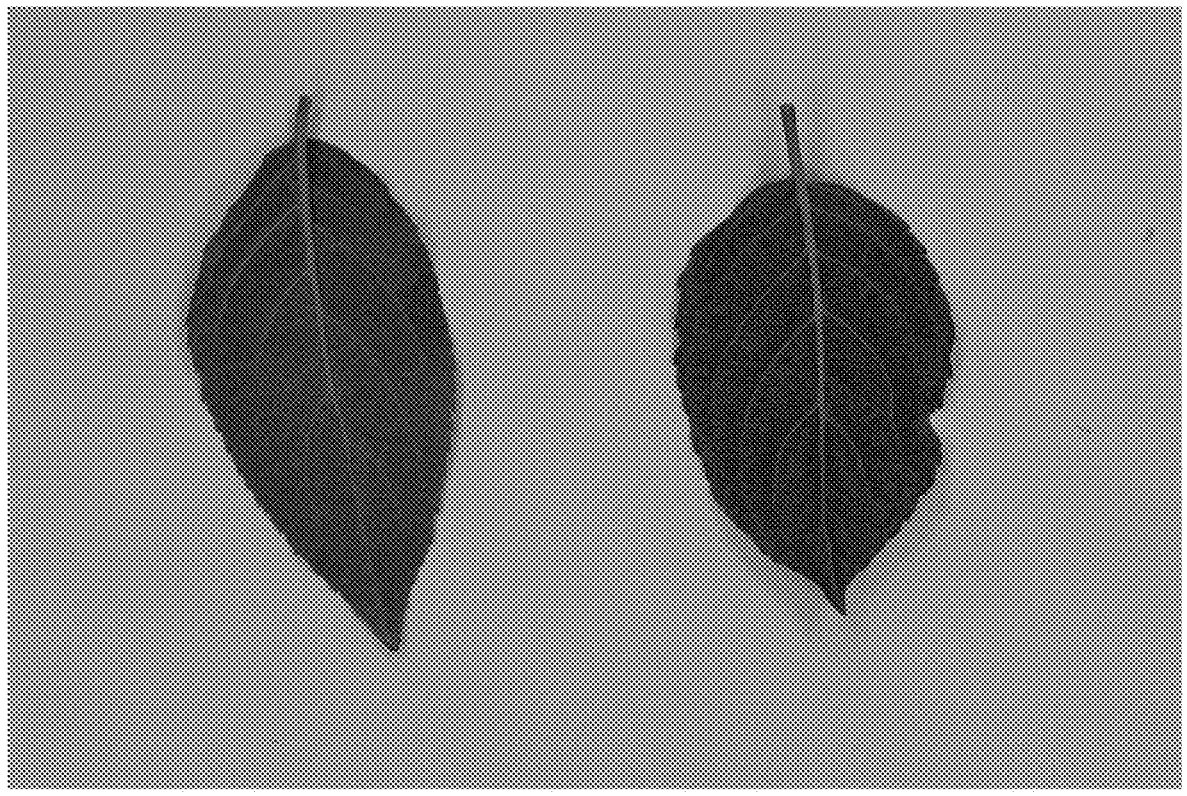
FIG. 18 shows thick durable, foliage of the 'SMNHPH' variety relative to foliage of a conventional *Hydrangea paniculata*.
Figure 19:
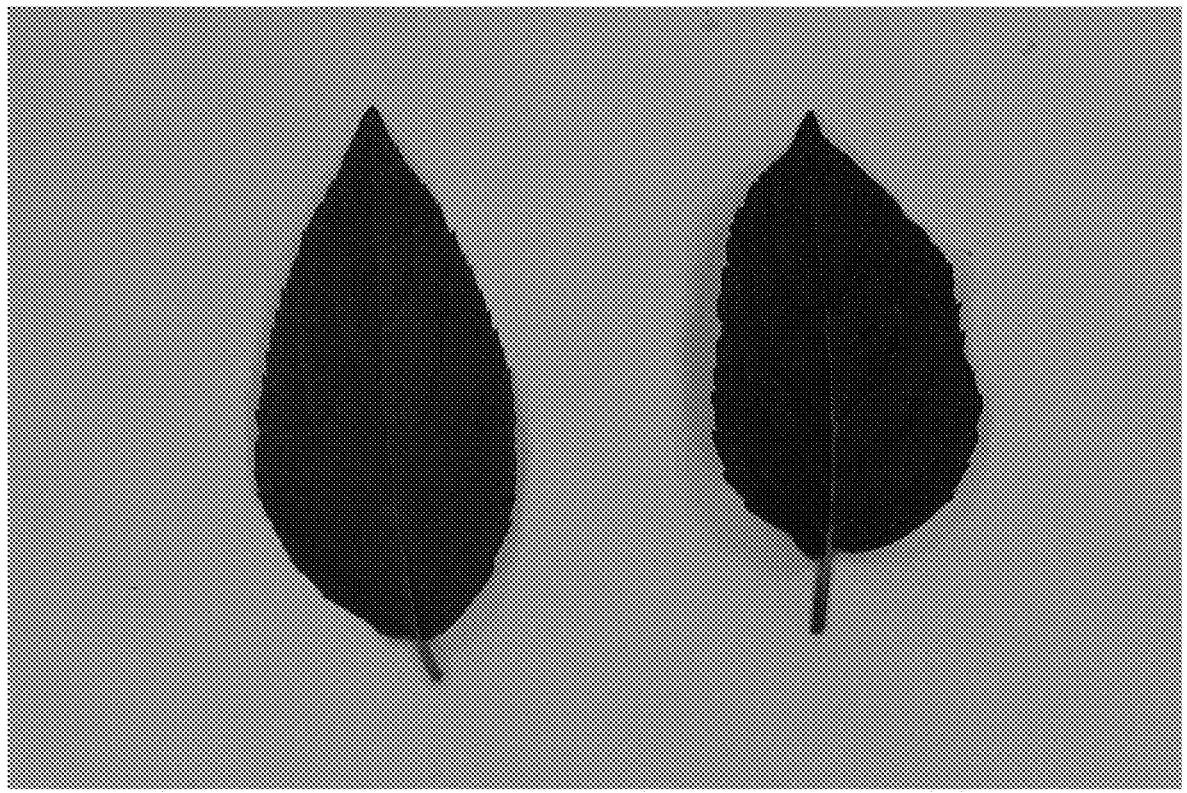
FIG. 19 shows another of thick, durable, foliage of the 'SMNHPH' variety relative to foliage of a conventional *Hydrangea paniculata*.

Yet another embodiment of the 'SMNHPH' variety or a *Hydrangea paniculata* bred according to the breeding methods described herein, or both, is thick, durable foliage. For instance, the leaves may be thicker and more puckered as opposed to the leaves of conventional *Hydrangea paniculata*, which have a flimsier feel and are smoother and less venial. A comparison of thicker, durable foliage of 'SMNHPH' relative to foliage of a conventional *Hydrangea paniculata* can be seen in FIGS. 18-19.

Figure 22:
FIG. 22 shows stem strength of the 'SMNHPH' variety relative to a conventional *Hydrangea paniculata*.
Figure 23:
FIG. 23 shows stem strength of the 'SMNHPH' variety relative to a 'RENHY' variety (PP20,670).

Another further embodiment of the 'SMNHPH' variety or a *Hydrangea paniculata* bred according to the breeding methods described herein, or both, is strong stems. For instance, the stems of the 'SMNHPH' variety may prevent the flower head from flopping or falling apart in a container, allowing the 'SMNHPH' variety to be bred or offered for sale, or both, without having to individually stake each branch to support the flower head. This strong stem aspect of the 'SMNHPH' variety can be seen in FIGS. 22 and 23 with the branches supporting the flower head in a container in a generally upright manner without stakes or external support. For comparison, two conventional *Hydrangea paniculata* are also shown in FIGS. 22 and 23 at an age similar to the 'SMNHPH' variety and with stems that flop entirely under the weight of the flower heads or spread out relative to the center of the plant under the weight of the flower heads. The strength of the stems of the 'SMNHPH' variety, in contrast, provides a plant with flower heads that are more upright than the conventional *Hydrangea paniculata*, yielding a plant that appears denser per the number of flower heads and that is more manageable for sale and breeding relative to conventional *Hydrangea paniculata*.

Another embodiment of the 'SMNHPH' variety or a *Hydrangea paniculata* bred according to the breeding methods described herein, or both, is orange fall color. Historically and in native populations, fall color of *Hydrangea paniculata* is yellow. Two conventional variety exist that exhibit red fall color 'SMNHPLQF' PP25,136 and 'BULK' PP16,812. However, orange fall color has not been observed in conventional cultivars of *Hydrangea paniculata*. The fall color of 'SMNHPH' begins with Greyed-red 178B then progresses to an Orange-Red 35A at outer tips of leaf and blends to Greyed-Orange 163C in interveinal.

It is to be understood that one or more embodiments according to the present disclosure may involve breeding, as described herein, to yield a *Hydrangea paniculata* having one or more traits of the 'SMNHPH' variety.

I. Botanical Description

In the following description, color references are made to the Royal Horticultural Society Color Chart 2015 except where general terms of ordinary dictionary significance are used. The following observations and measurements describe 'SMNHPH' plants grown in a commercial poly greenhouse in Grand Haven, Michigan under natural lighting. Measurements were taken during Summer of 2020. The plants were about 2.5 years old, growing in 3-gallon pots. The growing temperature ranged from 5° C. to 27° C. Measurements and numerical values represent averages of typical plant types.

Botanical classification: *Hydrangea paniculata* 'SMNHPH'
  Propagation
    Time to Initiate Roots: Approximately 18 days at about 18° to 27° C.
    Time to produce a rooted young plant: Approximately 60 days at about 18° to 27° C.
    Propagation Method: Softwood cuttings.
  Plant
  Plant type: Flowering deciduous perennial shrub.
  Growth Habit: Upward and outward.
  Overall Plant Shape: Upright, rounded, compact.
  Height: 68 cm.
  Plant Spread: 97 cm.
  Growth Rate: Good.
  Plant vigor: Moderate to vigorous.
  Branching Habit: Upright, outward.
  Length of Primary Lateral Branches: 55 cm.
  Diameter of Lateral Branches: 5 mm.
  Quantity of Lateral Branches: 30 to 40.
  Stem:
    Stem shape: Round.
    Stem strength: Strong.
    Color:
      Immature: RHS Grey-Brown N199C.
      Mature: RHS Grey-Brown 199B.
    Pubescence: None.
    Angle of attachment: 15° to 45°.
  Internode length: Average 3 cm.
  Root Description: Moderately dense, thick main roots with fine, fibrous secondary roots. Main roots colored near Brown 200D, secondary roots near Yellow-White 158D.
  Foliage
  Leaf:
    Arrangement: Opposite.
    Leaf shape: Elliptic.
    Average Length: 4.5 cm.
    Average Width: 3.75 cm.
    Apex: Cuspidate.
    Base: Obtuse.
    Margin: Serrate.
    Texture of top surface: Rough pubescent.
    Texture of bottom surface: Leathery with distinct veins.
    Color:
      Young foliage upper side: RHS Green 137B.
      Young foliage under side: RHS Yellow-Green 147B.
      Mature foliage upper side: RHS Green 137B.
      Mature foliage under side: RHS Yellow-Green 147D.
      Fall foliage upper side: RHS Orange-Red 35A.
      Fall foliage under side: RHS Orange-Red 35A.
    Venation:
      Pattern: Pinnate.
      Color upper side: RHS Yellow-Green 151C.
      Color under side: RHS Yellow-Green 145C.
      Fall color upper side: Greyed-Orange 163C.
      Fall color under side: Greyed-Orange 163C.
    Petiole:
      Average Length: 7 mm.
      Diameter: 2 mm.
      Petiole color upper side: RHS Green 143C slightly flushed Green-Purple 183C.
      Petiole color lower side: RHS Green 143C.
      Petiole Texture upper side: Smooth.
      Petiole Texture lower side: Slightly pubescent.
  Flower
  Natural flowering season: Summer until Fall.
  Inflorescence:
  Panicle:
    Shape: Very broad deltate.
    Height: 13 cm.
    Diameter: 11 cm.
    Quantity of flowers per inflorescence:
      Fertile flowers: About 100.
      Sterile flowers: 200 to 500.
    Persistent or self-cleaning: Persistent, self-cleaning after several weeks.
    Longevity: Individual flowers stay fresh on the plant for about 2 weeks. Inflorescences are ornamental for several weeks.
    Fragrance: None detected.
  Sterile Flower:
    Bud shape: Globose.
    Bud length: 2 mm.
    Bud diameter: 2 mm.
    Bud color: RHS Green-White 157C.
    Flower aspect: Outward.
    Flower length: 5 mm.
    Flower Diameter: 5 mm.
    Flower shape: Cruciform.
    Persistence: Persistent.
  Sterile Flower Petals:
    Petal Arrangement: Cruciform.
    Quantity: 4.
    Length of petal: 2 mm.
    Width of petal: 1 mm.
    Apex: Acute.
    Shape of petal: Narrow deltate.
    Petal margin: Entire.
    Petal Base: Obtuse.
    Petal Texture: Smooth, upper and under side.
  Color:
    Upper surface at first opening: RHS Green-White 157D.
    Under surface at first opening: RHS Green-White 157D.
    Upper surface at maturity: RHS Green-White 157D.
    Under surface at maturity: RHS Green-White 157D.

Sterile Flower Sepal:
  Arrangement: Cruciform.
  Number: 4.
  Shape: Obovate.
  Tip: Obtuse.
  Base: Acute.
  Margin: Entire.
  Length: 1 cm.
  Width: 9 mm.
  Texture, Upper: Smooth.
  Texture, Lower: Smooth.
  Color:
    Upper surface at first opening: RHS Green-White 157D.
    Under surface at first opening: RHS Green-White 157D.
    Upper surface at maturity: RHS White 155A. Late Summer strongly flushed 61B. Maturing to have a flush near Greyed-Purple 186 and 186D.
    Under surface at maturity: RHS White 155A. Late Summer strongly flushed 59D. Maturing to have a flush near Red-Purple 63B.
    Upper surface, at most mature: RHS Greyed-Purple 186 and 186D
    Under surface, at most mature: RHS Greyed-Purple 186 and 186D.
Sterile Flower Pedicel:
  Length: 1.5 cm.
  Diameter: 1 mm.
  Angle: 90-130°.
  Strength: Flexible.
  Texture: Some pubescence.
  Color: RHS Greyed-Green 193C.
Fertile Flower:
  Shape: Rotate.
  Depth: 5 mm.
  Diameter: 7 mm.
  Flower aspect: Outward.
  Persistence: Self-Cleaning.
  Longevity: 1-2 weeks.
  Bud shape: Orbicular.
  Bud length: 3 mm.
  Bud diameter. 3 mm.
  Bud texture: Glabrous.
  Bud color: RHS Green-White 157C.
Fertile Flower Petals:
  Arrangement: Rotate to cruciform.
  Quantity: 4.
  Length of petal: 3 mm.
  Width of petal: 2 mm.
  Apex: Acute.
  Shape of petal: Elliptic.
  Petal margin: Entire.
  Petal base: Truncate.
  Petal Texture: Smooth, upper and under side.
Color:
  Upper surface at first opening: RHS White 155C.
  Under surface at first opening: RHS White 155C.
  Upper surface at maturity: RHS White 155C.
  Under surface at maturity: RHS White 155C.
Fertile Flower Sepal:
  Arrangement: Cruciform.
  Quantity: 4.
  Length: 1 mm.
  Width: 1 mm.
  Apex: Obtuse.
  Shape: Orbicular.
  Margin: Entire.
  Base: Truncate.
  Texture: Smooth, upper and under side.
  Color:
    Upper surface at first opening: RHS Yellow-Green 145C.
    Under surface at first opening: RHS Yellow-Green 145C.
    Upper surface at maturity: RHS Yellow-Green 145C.
    Under surface at maturity: RHS Yellow-Green 145C.
Fertile Flower Pedicel:
  Angle: 90° to 130°.
  Strength: Moderate.
  Length: 5 mm.
  Width: 1 mm.
  Texture: Slight pubescence.
  Color: RHS White 155C.
Reproductive Organs
Sterile flowers Androecium: Present.
Stamens: 6 to 0 mm, Inconspicuous, about 1 mm.
Filament: Colored near White NN155A.
Anthers: Less than 1 mm long, colored near White NN155A.
Sterile flowers Gynoecium: Not present.
Fertile flowers:
Stamens:
Number: 8.
Filament length: 3 mm.
Filament color: RHS White 155C.
Anthers:
  Shape: Globular.
  Length: <1 mm.
  Color: RHS White 155C.
  Pollen color: RHS White 155c.
  Pollen amount: Moderate.
Pistil:
  Number: 1.
  Length: Less than 1 mm.
  Style:
  Length: About 0.5 mm
  Color: RHS Yellow-Green 145D.
  Stigma:
    Shape: Lobed.
    Color: RHS Yellow-Green 145D.
Other Characteristics
Seeds and fruits: None observed.
Disease/pest resistance: Neither resistance nor susceptibility to normal diseases and pests of *Hydrangea* have been observed.
Temperature tolerance: USDA Zones 3 to 9.

II. Using *Hydrangea paniculata* Plants to Develop Other *Hydrangea paniculata* Plants The *Hydrangea paniculata* plants herein, including the 'SMNHPH' variety, can also provide a source of breeding material that may be used to develop new *Hydrangea paniculata* plants and varieties. Plant breeding techniques known in the art and used in a *Hydrangea paniculata* plant breeding program include, but are not limited to, recurrent selection, mass selection, bulk selection, hybridization, mass selection, backcrossing, pedigree breeding, open-pollination breeding, restriction fragment length polymorphism enhanced selection, genetic marker enhanced selection, making double haploids, mutagenesis and transformation. Often combinations of these techniques may be implemented. There are many analytical methods available to evaluate a new variety. For instance, the observation of phenotypic traits or genotypic analysis, or both, may be used.

III. Additional Breeding Methods

Any plants produced using the *Hydrangea paniculata* plants disclosed in the present application, including the 'SMNHPH' variety, and at least one parent are also an embodiment. Several methods of breeding the *Hydrangea paniculata* are described herein, but it is to be understood that the present disclosure is not so limited. Any type of breeding methodology may be implemented.

Descriptions of breeding methods can be found in one of several reference books (e.g., Allard, "Principles of Plant Breeding" (1999); Vainstein, "Breeding for Ornamentals: Classical and Molecular Approaches," Kluwer Academic Publishers (2002); Callaway, "Breeding Ornamental Plants," Timber Press (2000); and Bragdo, Marie, "Interspecific Crosses in *Lupinus*: Cytology and Inheritance of Flower Color," Institute of Genetics and Plant Breeding, Agricultural College of Norway, Vollebekk, Norway (Sep. 28, 1956)).

Breeding steps that may be used in the *Hydrangea paniculata* plant breeding program can include for example, pedigree breeding, backcrossing, mutation breeding, and recurrent selection. In conjunction with these steps, techniques such as RFLP-enhanced selection, genetic marker enhanced selection (for example, SSR markers), and the making of double haploids may be utilized.

As used herein, the term "plant" includes plant cells, plant protoplasts, plant cell tissue cultures from which *Hydrangea paniculata* plants can be regenerated, plant calli, plant clumps, and plant cells that are intact in plants or parts of plants, such as pollen, ovules, embryos, protoplasts, meristematic cells, callus, leaves, anthers, cotyledons, hypocotyl, pistils, roots, root tips, seeds, flowers, petiole, shoot, or stems and the like.

A. Pedigree Breeding

Pedigree breeding starts with the crossing of two genotypes, such as a *Hydrangea paniculata* described herein, including the 'SMNHPH' variety, and another different *Hydrangea paniculata* having one or more desirable characteristics that is lacking or which complements a *Hydrangea paniculata* described herein. If the two original parents do not provide all the desired characteristics, other sources can be included in the breeding population. In the pedigree method, superior plants are selfed and selected in successive filial generations. In the succeeding filial generations, the heterozygous condition gives way to homogeneous varieties as a result of self-pollination and selection. In the pedigree method of breeding, five or more successive filial generations of selfing and selection may be practiced: $F_1$ to $F_2$; $F_2$ to $F_3$; $F_3$ to $F_4$; $F_4$ to $F_5$; etc. After a sufficient amount of inbreeding, successive filial generations may serve to increase seed of the developed variety. The developed variety may include homozygous alleles at about 95% or more of its loci.

B. Backcross Breeding

Backcross breeding has been used to transfer genes for a simply inherited, highly heritable trait into a target homozygous variety or inbred line which is the recurrent parent. The source of the trait to be transferred is called the donor parent. After the initial cross, individuals possessing the phenotype of the donor parent are selected and repeatedly crossed (backcrossed) to the recurrent parent. The resulting plant is expected to have the attributes of the recurrent parent and the desirable trait transferred from the donor parent.

In addition to being used to create a backcross conversion, backcrossing can also be used in combination with pedigree breeding. As discussed previously, backcrossing can be used to transfer one or more target traits from one variety, the donor parent, to a developed variety called the recurrent parent, which has commercial characteristics of interest and yet lacks that target trait or traits. However, the same procedure can be used to move the progeny toward the genotype of the recurrent parent, but at the same time retain many components of the nonrecurrent parent by stopping the backcrossing at an early stage and proceeding with selfing and selection. For example, a *Hydrangea paniculata* plant may be crossed with another variety to produce a first-generation progeny plant. The first-generation progeny plant may then be backcrossed to one of its parent varieties to create a $BC_1$ or $BC_2$. Progeny are selfed and selected so that the newly developed variety has many of the attributes of the recurrent parent and yet several of the desired attributes of the nonrecurrent parent. This approach leverages the value and strengths of the recurrent parent for use in new *Hydrangea paniculata* varieties.

Therefore, another embodiment is a method of making a backcross conversion of a *Hydrangea paniculata* described herein, including the 'SMNHPH' variety, comprising the steps of crossing a *Hydrangea paniculata* with a donor plant comprising a desired trait, selecting an $F_1$ progeny plant comprising the desired trait, and backcrossing the selected $F_1$ progeny plant to a plant of *Hydrangea paniculata* described herein, including the 'SMNHPH' variety. This method may further comprise the step of obtaining a molecular marker profile of a *Hydrangea paniculata* described herein and using the molecular marker profile to select for a progeny plant with the desired trait and the molecular marker profile of a *Hydrangea paniculata* described herein.

C. Recurrent Selection and Mass Selection

Recurrent selection is a method used in a plant breeding program to improve a population of plants. A *Hydrangea paniculata* described herein, including the 'SMNHPH' variety, may be suitable for use in a recurrent selection program. The method entails individual plants cross-pollinating with each other to form progeny. The progenies are grown and the superior progenies selected by any number of selection methods, which include individual plant, half-sib progeny, full-sib progeny, and selfed progeny. The selected progenies are cross-pollinated with each other to form progeny for another population. This population is planted and again superior plants are selected to cross-pollinate with each other. Recurrent selection is a cyclical process and therefore can be repeated as many times as desired. The objective of recurrent selection is to improve the traits of a population. The improved population can then be used as a source of breeding material to obtain new varieties for commercial or breeding use, including the production of a synthetic variety. A synthetic variety is the resultant progeny formed by the intercrossing of several selected varieties.

Mass selection is a useful technique when used in conjunction with molecular marker enhanced selection. In mass selection, seeds from individuals are selected based on phenotype or genotype. These selected seeds are then bulked and used to grow the next generation. Bulk selection may involve growing a population of plants in a bulk plot, allowing the plants to self-pollinate, harvesting the seed in bulk, and then using a sample of the seed harvested in bulk to plant the next generation. Also, instead of self-pollination, directed pollination could be used as part of the breeding program.

Mass and recurrent selections can be used to improve populations of either self- or cross-pollinating plants. A genetically variable population of heterozygous individuals is either identified, or created, by intercrossing several different parents. The best plants, or plants satisfying target criteria, may be selected based on individual superiority, outstanding progeny, or excellent combining ability. The selected plants are intercrossed to produce a new population in which further cycles of selection are continued.

D. Mutation Breeding

Mutation breeding is another method of introducing new traits into a *Hydrangea paniculata* according to one embodiment herein, including the 'SMNHPH' variety. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation; such as X-rays, Gamma rays (e.g., cobalt 60 or cesium 137), neutrons, (product of nuclear fission by uranium 235 in an atomic reactor), Beta radiation (emitted from radioisotopes such as phosphorus 32 or carbon 14), or ultraviolet radiation (preferably from 2500 to 2900 nm), or chemical mutagens (such as base analogues (5-bromo-uracil)), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines. Once a desired trait is observed through mutagenesis the trait may then be incorporated into existing germplasm by traditional breeding techniques. Details of mutation breeding can be found in Vainstein, "Breeding for Ornamentals: Classical and Molecular Approaches," Kluwer Academic Publishers (2002). In addition, mutations created in other *Hydrangea paniculata* plants may be used to produce a backcross conversion of a *Hydrangea paniculata* described herein, including the 'SMNHPH' variety, that comprises such mutation.

Additional methods include, but are not limited to, expression vectors introduced into plant tissues using a direct gene transfer method, such as microprojectile-mediated delivery, DNA injection, electroporation, and the like. More preferably, expression vectors are introduced into plant tissues by using either microprojectile-mediated delivery with a biolistic device or by using *Agrobacterium*-mediated transformation. Transformant plants obtained with the protoplasm of the subject *Hydrangea paniculata* plants are intended to be within the scope of the embodiments of the application.

E. Single-Gene Conversions

When the term *Hydrangea paniculata* plant is used in the context of an embodiment of the present application, this also includes any single gene conversions of a *Hydrangea paniculata* described herein. The term single gene converted plant as used herein refers to those *Hydrangea paniculata* plants which are developed by a plant breeding technique called backcrossing wherein all or nearly all of the target morphological and physiological characteristics of a variety are recovered in addition to the single gene transferred into the variety via the backcrossing technique. Backcrossing methods can be used with one embodiment of the present application to improve or introduce a characteristic into the variety. The term "backcrossing" as used herein refers to the repeated crossing of a hybrid progeny back to the recurrent parent, i.e., backcrossing 1, 2, 3, 4, 5, 6, 7, 8, or more times to the recurrent parent. The parental *Hydrangea paniculata* that contributes the gene for the target characteristic is termed the nonrecurrent or donor parent. This terminology refers to the fact that the nonrecurrent parent is used one time in the backcross protocol and therefore does not recur. The parental *Hydrangea paniculata* plant to which the gene or genes from the nonrecurrent parent are transferred is known as the recurrent parent as it is used for several rounds in the backcrossing protocol (Poehlman & Sleper (1994). In one backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a *Hydrangea paniculata* plant is obtained wherein all or nearly all of the target morphological and physiological characteristics of the recurrent parent are recovered in the converted plant, in addition to the single transferred gene from the nonrecurrent parent.

The selection of a suitable recurrent parent according to target criteria may provide for a successful backcrossing procedure. The goal of a backcross protocol is to alter or substitute a single trait or characteristic in the original variety. To accomplish this, a single gene of the recurrent variety is modified or substituted with the desired gene from the nonrecurrent parent, while retaining all or nearly all of the rest of the target genetics, and therefore the target physiological and morphological constitution of the original variety. The choice of the particular nonrecurrent parent may depend on the purpose of the backcross; one of the major purposes is to add some commercial trait or traits of interest to the plant. The exact backcrossing protocol may depend on the characteristic or trait being altered to determine an appropriate testing protocol. Although backcrossing methods may be simplified when the characteristic being transferred is a dominant allele, a recessive allele may also be transferred. In this instance, the breeding process may involve introduction of a test of the progeny to determine if the target characteristic has been successfully transferred.

Many single gene traits have been identified that are not regularly selected in the development of a new variety but that can be improved by backcrossing techniques.

F. Introduction of a New Trait or Locus into the *Hydrangea paniculata* Described Herein

*Hydrangea paniculata* described herein represent a new base of genetics into which a new locus or trait may be introgressed. Direct transformation and backcrossing represent two methods that can be used to accomplish such an introgression. The terms "backcross conversion" and "single locus conversion" are used interchangeably to designate the product of a backcrossing program.

G. Transformation

Transformation methods include, but are not limited to, expression vectors introduced into plant tissues using a gene transfer method, such as microprojectile-mediated delivery, DNA injection, electroporation, and the like. In some embodiments, expression vectors are introduced into plant tissues of a *Hydrangea paniculata* described herein, including the 'SMNHPH' variety, by using either microprojectile-mediated delivery with a biolistic device or by using *Agrobacterium*-mediated transformation. Accordingly, further embodiments are methods of transformation using a *Hydrangea paniculata* described herein and the transformant plants obtained with the protoplasm of the subject *Hydrangea paniculata* plants.

1. Expression Vectors for 'SMNHPH' Transformation: Marker Genes

Plant transformation may involve the construction of an expression vector which will function in plant cells. Such expression vectors comprise DNA comprising a gene under control of, or operatively linked to, a regulatory element (e.g., a promoter). Expression vectors may include at least one genetic marker operably linked to a regulatory element that allows transformed cells containing the marker to be either recovered by negative selection (e.g., inhibiting growth of cells that do not contain the selectable marker gene) or by positive selection (e.g., screening for the product encoded by the genetic marker). Selectable marker genes used for plant transformation may include, for example, genes that code for enzymes that metabolically detoxify a selective chemical agent which may be an antibiotic or a herbicide, or genes that encode an altered target which is insensitive to the inhibitor. Positive selection methods may also be used.

One selectable marker gene used for plant transformation is the neomycin phosphotransferase II (nptII) gene which, when under the control of plant regulatory signals, confers resistance to kanamycin. Another selectable marker gene used for plant transformation is the hygromycin phosphotransferase gene which confers resistance to the antibiotic hygromycin.

Selectable marker genes for plant transformation not of bacterial origin include, for example, mouse dihydrofolate reductase, plant 5-enolpyruvylshikimate-3-phosphate synthase, and plant acetolactate synthase. See, e.g., Eichholtz, et al., SOMATIC CELL MOL. GENET., 13:67 (1987); Shah, et al., SCIENCE, 233:478 (1986); and Charest, et al., PLANT CELL REP., 8:643 (1990).

Another class of marker genes for plant transformation involves screening of presumptively transformed plant cells. Reporter genes are an example of this type of marker genes and can be used to quantify or visualize the spatial pattern of expression of a gene in specific tissues. Moreover, reporter genes can be fused to a gene or gene regulatory sequence for the investigation of gene expression. Marker genes used for screening presumptively transformed cells include β-glucuronidase (GUS), β-galactosidase, luciferase, and chloramphenicol acetyltransferase. See, e.g., Teeri, et al., EMBO J., 8:343 (1989); Koncz, et al., PROC. NATL. ACAD. SCI. USA, 84:131 (1987); and DeBlock, et al., EMBO J., 3:1681 (1984).

2. Expression Vectors for 'SMNHPH' Transformation: Promoters

Genes included in expression vectors must be driven by a nucleotide sequence comprising a regulatory element (e.g., a promoter). Many types of promoters may be used, as are other regulatory elements that can be used alone or in combination with promoters.

Some promoters are under developmental control and include promoters that preferentially initiate transcription in certain tissues, such as leaves, roots, seeds, fibers, xylem vessels, tracheids, or sclerenchyma. Such promoters may be referred to as "tissue-preferred" whereas promoters that initiate transcription only in a certain tissue may be referred to as "tissue-specific." A "cell-type" specific promoter primarily drives expression in certain cell types in one or more organs, for example, vascular cells in roots or leaves. Whereas an "inducible" promoter may refers to a promoter which is under environmental control. Examples of environmental conditions that may affect transcription by inducible promoters include anaerobic conditions or the presence of light. Tissue-specific, tissue-preferred, cell-type specific, and inducible promoters constitute the class of "non-constitutive" promoters. A "constitutive" promoter refers to a promoter that is active under most environmental conditions. Many types of promoters may be used, such that it is to be understood the present disclosure is not limited to the promotors described and identified herein.

3. Additional Transformation Embodiments

The foregoing methods for transformation may be used for producing a transgenic variety. The transgenic variety could then be crossed with another (non-transformed or transformed) variety in order to produce a new transgenic variety. Alternatively, a genetic trait that has been engineered into a particular hydrangea line using the foregoing transformation techniques could be moved into another line using other breeding techniques. For example, a backcrossing approach could be used to move an engineered trait from a publically available variety into an elite variety, such as a *Hydrangea paniculata* described herein (including the 'SMNHPH' variety), or a backcrossing approach can be used to move a foreign gene from a variety containing the foreign gene in its genome into a variety that does not contain that gene.

Likewise, by means of such embodiments, genes of commercial interest can be expressed in transformed plants. More particularly, plants can be genetically engineered to express various phenotypes of commercial interest, including, but not limited to, genes that confer resistance to pests or disease, genes that confer resistance to an herbicide, genes that confer or contribute to a value-added or desired trait, genes that control male sterility, genes that create a site-for-site specific DNA integration, and genes that affect abiotic stress resistance. Many different genes are known and could potentially be introduced into a *Hydrangea paniculata* according to one embodiment described in the present disclosure. Non-limiting examples of particular genes and corresponding phenotypes one may choose to introduce into a *hydrangea paniculata* plant include one or more genes for insect tolerance, such as a *Bacillus thuringiensis* (Bt.) gene, pest tolerance such as genes for fungal disease control, herbicide tolerance such as genes conferring glyphosate tolerance, and genes for quality improvements such as environmental or stress tolerances, or any desirable changes in plant physiology, growth, development, morphology, or plant product(s). For example, structural genes would include any gene that confers insect tolerance including but not limited to a *Bacillus* insect control protein gene as described in International Publication No. WO 99/31248, U.S. Pat. Nos. 5,689,052, 5,500,365 and 5,880,275. In another embodiment, the structural gene can confer tolerance to the herbicide glyphosate as conferred by genes including, but not limited to *Agrobacterium* strain CP4 glyphosate resistant EPSPS gene (aroA:CP4) as described in U.S. Pat. No. 5,633,435, or glyphosate oxidoreductase gene (GOX) as described in U.S. Pat. No. 5,463,175. Alternatively, the DNA coding sequences can affect these phenotypes by encoding a non-translatable RNA molecule that causes the targeted inhibition of expression of an endogenous gene, for example via antisense- or cosuppression-mediated mechanisms. The RNA could also be a catalytic RNA molecule (e.g., a ribozyme) engineered to cleave a desired endogenous mRNA product. See, e.g., Gibson and Shillito, *MOL. BIOTECH.*, 7:125, 1997. Thus, any gene which produces a protein or mRNA which is necessary for a phenotype or morphology change of interest is useful for the practice of one or more embodiments described in the present disclosure.

H. Backcross Conversions of *Hydrangea paniculata*

A backcross conversion of the *Hydrangea paniculata* described herein occurs when DNA sequences are introduced through backcrossing (Allard, "Principles of Plant Breeding" (1999)) with the *Hydrangea paniculata* described herein being utilized as the recurrent parent. Both naturally occurring and transgenic DNA sequences may be introduced through backcrossing techniques. A backcross conversion may produce a plant with a trait or locus conversion in at least two or more backcrosses, including at least 2 crosses, at least 3 crosses, at least 4 crosses, at least crosses, and the like. Molecular marker assisted breeding or selection may be utilized to reduce the number of backcrosses necessary to achieve the backcross conversion. For example, see, Openshaw, S. J., et al., Marker-assisted Selection in Backcross Breeding, Proceedings Symposium of the Analysis of Molecular Data, Crop Science Society of America, Corvallis, Oreg. (August 1994), where it is demonstrated that a backcross conversion can be made in as few as two backcrosses.

The complexity of the backcross conversion method depends on the type of trait being transferred (single genes or closely linked genes as compared to unlinked genes), the level of expression of the trait, the type of inheritance (cytoplasmic or nuclear), and the types of parents included in the cross. It is to be understood that for single gene traits that are relatively easy to classify, the backcross method is effective and manageable. See, Allard, "Principles of Plant Breeding" (1999). Target traits that may be transferred through backcross conversion include, but are not limited to, sterility (nuclear and cytoplasmic), fertility restoration, drought tolerance, nitrogen utilization, ornamental features, disease resistance (bacterial, fungal, or viral), insect resistance, and herbicide resistance. In addition, an introgression site itself, such as an FRT site, Lox site, or other site specific integration site, may be inserted by backcrossing and utilized for direct insertion of one or more genes of interest into a specific plant variety. In some embodiments, the number of loci that may be backcrossed into a *Hydrangea paniculata* described herein is at least 1, 2, 3, 4, or 5, and/or no more than 6, 5, 4, 3, or 2. A single locus may contain several transgenes, such as a transgene for disease resistance that, in the same expression vector, also contains a transgene for herbicide resistance. The gene for herbicide resistance may be used as a selectable marker and/or as a phenotypic trait. A single locus conversion of site specific integration system allows for the integration of multiple genes at the converted loci.

The backcross conversion may result from either the transfer of a dominant allele or a recessive allele. Selection of progeny containing the trait of interest is accomplished by direct selection for a trait associated with a dominant allele. Transgenes or genes transferred via backcrossing typically function as a dominant single gene trait and are relatively easy to classify. Selection of progeny for a trait that is transferred via a recessive allele requires growing and selfing the first backcross generation to determine which plants carry the recessive alleles. Recessive traits may involve additional progeny testing in successive backcross generations to determine the presence of the locus of interest. The last backcross generation may be selfed to give pure breeding progeny for the gene(s) being transferred, although a backcross conversion with a stably introgressed trait may also be maintained by further backcrossing to the recurrent parent with selection for the converted trait.

I. Molecular Techniques Using *Hydrangea paniculata* Described Herein

Molecular biological techniques may allow the isolation and characterization of genetic elements with specific functions. Molecular techniques include transformation. See Vainstein, "Breeding for Ornamentals: Classical and Molecular Approaches," Kluwer Academic Publishers (2002).

1. Breeding with Molecular Markers

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select for the genome of the recurrent parent and against the genome of the donor parent. Using this procedure can minimize or reduce the amount of genome from the donor parent that remains in the selected plants. It can also be used to reduce the number of crosses back to the recurrent parent needed in a backcrossing program. The use of molecular markers in the selection process is often called genetic marker enhanced selection. Molecular markers may also be used to identify and exclude certain sources of germplasm as parental varieties or ancestors of a plant by providing a means of tracking genetic profiles through crosses. Molecular markers, which includes markers identified through the use of techniques such as Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs), and Single Nucleotide Polymorphisms (SNPs), may be used in plant breeding methods in connection with a *Hydrangea paniculata* described herein, including the 'SMNHPH' variety. See Vainstein, "Breeding for Ornamentals: Classical and Molecular Approaches," Kluwer Academic Publishers (2002).

2. Genetic Marker Profile Through SSR and First Generation Progeny

In addition to phenotypic observations, a plant can also be identified by its genotype. The genotype of a plant can be characterized through a genetic marker profile which can identify plants of the same variety, or a related variety, or be used to determine or validate a pedigree. Genetic marker profiles can be obtained by techniques such as Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) (which are also referred to as Microsatellites), and Single Nucleotide Polymorphisms (SNPs).

3. Signal Sequences for Targeting Proteins to Subcellular Compartments

Transport of a protein produced by a transgene to a sub cellular compartment, such as the chloroplast, vacuole, peroxisome, glyoxysome, cell wall, or mitochondrion, or for secretion into the apoplast, may be accomplished by means of operably linking a nucleotide sequence encoding a signal sequence (targeting sequence) typically to the 5' and/or 3' region of the transgene encoding the protein of interest. Signal sequences are well-known in the art. See, e.g., Becker, et al., PLANT MOL. BIOL., 20:49 (1992); Knox, et al., PLANT MOL. BIOL., 9:3-17 (1987); Lerner, et al., PLANT PHYSIOL., 91:124-129 (1989); Frontes, et al., PLANT CELL, 3:483-496 (1991); Matsuoka, et al., PROC. NATL. ACAD. SCI., 88:834 (1991); Gould, et al., J. CELL. BIOL., 108:1657 (1989); Creissen, et al., PLANT J., 2:129 (1991); Kalderon, et al., CELL, 39:499-509 (1984); and Steifel, et al., PLANT CELL, 2:785-793 (1990).

4. Gene Silencing

Techniques for gene silencing may be utilized, including, but not limited to, knock-outs (such as by insertion of a transposable element such as Mu) or other genetic elements such as a FRT, Lox, or other site specific integration sites; antisense technology; co-suppression; RNA interference; virus-induced gene silencing; target-RNA-specific ribozymes; hairpin structures; MicroRNA; ribozymes; oligonucleotide mediated targeted modification; Zn-finger targeted molecules; CRISPR/Cas9 system; and other methods or combinations of the above. See, e.g., Sheehy, et al., PNAS USA, 85:8805-8809 (1988); U.S. Pat. Nos. 5,107,065; 5,453,566; 5,759,829; Jorgensen, TRENDS BIOTECH., 8(12):340-344 (1990); Flavell, PNAS USA, 91:3490-3496 (1994); Neuhuber, et al., MOL. GEN. GENET., 244:230-241 (1994); Napoli, et al., PLANT CELL, 2:279-289 (1990); U.S. Pat. No. 5,034,323; Sharp, GENES DEV., 13:139-141 (1999); Zamore, et al., CELL, 101:25-33 (2000); Montgomery, et al., PNAS USA, 95:15502-15507 (1998); Burton, et al., PLANT CELL, 12:691-705 (2000); Baulcombe, CURR. OP. PLANT BIO., 2:109-113 (1999); Haseloff, et al., NATURE, 334:585-591 (1988); Smith, et al., NATURE, 407:319-320 (2000); U.S. Pat. Nos. 6,423,885; 7,138,565; 6,753,139; 7,713,715; Aukerman & Sakai, PLANT CELL, 15:2730-2741 (2003); Steinecke, et al., EMBO J., 11:1525 (1992); Perriman, et al., ANTISENSE RES. DEV., 3:253 (1993); U.S. Pat. Nos. 6,528,700; 6,911,575; 7,151,201; 6,453,242; 6,785,613; 7,177,766; 7,788,044; International Publication No. WO2014/068346; Martinelli, et al., *Proposal of a Genome Editing System for Genetic Resistance to Tomato Spotted Wilt Virus* 2014 AMERICAN JOURNAL OF APPLIED SCIENCES; Noman, et al., *CRISPR-Cas9: Tool for Qualitative and Quantitative Plant Genome Editing*, November 2016 FRONTIERS IN PLANT SCIENCE Vol. 7; and Zhang et al., *Exploiting the CRISPR/Cas9 System for Targeted Genome Mutagenesis in Petunia* February 2016 SCIENCE REPORTS Volume 6.

J. Tissue Culture

Further reproduction of the variety can occur by tissue culture and regeneration. Tissue culture of various tissues of ornamental plants and a *Hydrangea paniculata* described herein and regeneration of plants therefrom may be utilized in breeding. For example, reproduction or breeding can be conducted according to one or more embodiments described in the following: Valla Rego, Luciana et al., Crop Breeding and Applied Technology. 1(3): 283-300 (2001); Komatsuda, T., et al., Crop Sci., 31:333-337 (1991); Stephens, P. A., et al., *Theor. Appl. Genet.*, 82:633-635 (1991); Komatsuda, T., et al., *Plant Cell, Tissue and Organ Culture*, 28:103-113 (1992); Dhir, S., et al., *Plant Cell Reports*, 11:285-289 (1992); Pandey, P., et al., *Japan J. Breed.*, 42:1-5 (1992); and Shetty, K., et al., Plant Science, 81:245-251(1992). Thus, another embodiment is to provide cells which upon growth and differentiation produce *Hydrangea paniculata* plants having one or more physiological and morphological characteristics of a *Hydrangea paniculata* described in the present application, including the 'SMNHPH' variety.

Regeneration refers to the development of a plant from tissue culture. The term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as pollen, ovules, embryos, protoplasts, meristematic cells, callus, leaves, anthers, cotyledons, hypocotyl, pistils, roots, root tips, flowers, seeds, petiole, shoot, or stems, and the like.

K. Targeted Gene Editing

Targeted gene editing can be done using CRISPR/Cas9 technology (Saunders & Joung, *Nature Biotechnology*, 32, 347-355, 2014). CRISPR is a type of genome editing system that stands for Clustered Regularly Interspaced Short Palindromic Repeats. This system and CRISPR-associated (Cas) genes enable organisms, such as select bacteria and archaea, to respond to and eliminate invading genetic material. (Ishino, Y., et al. *J. Bacteriol.* 169, 5429-5433 (1987)). These repeats were known as early as the 1980s in *E. coli*, but Barrangou and colleagues demonstrated that *S. thermophilus* can acquire resistance against a bacteriophage by integrating a fragment of a genome of an infectious virus into its CRISPR locus. (Barrangou, R., et al. *Science* 315, 1709-1712 (2007)). Many plants have already been modified using the CRISPR system. See for example, U.S. Application Publication No. WO2014068346 (Gyorgy et al., Identification of a *Xanthomonas euvesicatoria* resistance gene from pepper (*Capsicum annuum*) and method for generating plants with resistance), Martinelli, F. et al., "Proposal of a Genome Editing System for Genetic Resistance to Tomato Spotted Wilt Virus" *American Journal of Applied Sciences* 2014, and Noman, A. et al., and "CRISPR-Cas9: Tool for Qualitative and Quantitative Plant Genome Editing" *Frontiers in Plant Science Vol.* 7 Nov. 2016.

Gene editing can also be done using crRNA-guided surveillance systems for gene editing. Additional information about crRNA-guided surveillance complex systems for gene editing can be found in the following documents, which are incorporated by reference in their entirety: U.S. Application Publication No. 2010/0076057 (Sontheimer et al., Target DNA Interference with crRNA); U.S. Application Publication No. 2014/0179006 (Feng, CRISPR-CAS Component Systems, Methods, and Compositions for Sequence Manipulation); U.S. Application Publication No. 2014/0294773 (Brouns et al., Modified Cascade Ribonucleoproteins and Uses Thereof); Sorek et al., *Annu. Rev. Biochem.* 82:273-266, 2013; and Wang, S. et al., *Plant Cell Rep* (2015) 34: 1473-1476. Therefore, it is another embodiment to use the CRISPR system on a *Hydrangea paniculata* of the instant application to, for example, modify traits and tolerances to pests and viruses.

Directional terms, such as "vertical," "horizontal," "top," "bottom," "upper," "lower," "inner," "inwardly," "outer" and "outwardly," are used to assist in describing the invention based on the orientation of the embodiments shown in the illustrations. The use of directional terms should not be interpreted to limit the invention to any specific orientation (s).

The above description is that of current embodiments of the invention. Various alterations and changes can be made without departing from the spirit and broader aspects of the invention as defined in the appended claims, which are to be interpreted in accordance with the principles of patent law including the doctrine of equivalents. This disclosure is presented for illustrative purposes and should not be interpreted as an exhaustive description of all embodiments of the invention or to limit the scope of the claims to the specific elements illustrated or described in connection with these embodiments. For example, and without limitation, any individual element(s) of the described invention may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Further, the disclosed embodiments include a plurality of features that are described in concert and that might cooperatively provide a collection of benefits. The present invention is not limited to only those embodiments that include all of these features or that provide all of the stated benefits, except to the extent otherwise expressly set forth in the issued claims. Any reference to claim elements in the singular, for example, using the articles "a," "an," "the" or "said," is not to be construed as limiting the element to the singular.

DEPOSIT INFORMATION

A deposit of *Hydrangea* variety 'SMNHPH' has been made with and accepted under the Budapest Treaty by the International Depository Authority of Provasoli-Guillard National Center for Marine Algae and Microbiota (NCMA) at Bigelow Laboratory for Ocean Science (60 Bigelow Drive, East Boothbay, Me. 04544), on Mar. 14, 2023 under NCMA Accession number 202303015. The deposit will be maintained in the NCMA depository for a period of 30 years, or years after the most recent request, or for the enforceable life of the patent, whichever is longer, and will be replaced if necessary, during that period. Upon issuance, all restrictions on the availability to the public of the deposit will be irrevocably removed consistent with all of the requirement of 37 C.F.R. §§ 1.801-1.809.

The embodiments of the invention in which an exclusive property or privilege is claimed are defined as follows:

1. A hydrangea plant of variety 'SMNHPH', wherein a representative sample of plant tissue of said variety was deposited under NCMA Accession number 202303015.

2. A tissue or cell culture produced from the plant of claim 1.

3. A method of developing a hydrangea plant variety having the physiological and morphological characteristics of a hydrangea plant of variety 'SMNHPH', wherein a representative sample of plant tissue of said variety was deposited under NCMA Accession number 202303015, said method comprising:
   genotyping a hydrangea plant of variety 'SMNHPH', wherein said genotyping includes obtaining a sample of nucleic acids from the plant and detecting in the nucleic acids a plurality of polymorphisms, and using the identified polymorphisms for marker-assisted selection in a breeding program.

4. A method for developing a hydrangea plant variety comprising one or more of:
   a) identifying and selecting a spontaneous mutation of a hydrangea plant of variety 'SMNHPH' or a part thereof, and cultivating the selected spontaneous mutation plant or plant part;
   b) introducing a mutation into the genome of a plant of variety 'SMNHPH' or a part thereof, and cultivating said mutated plant or plant part; or
   c) transforming a hydrangea plant of variety 'SMNHPH' with a transgene;
   wherein a representative sample of plant tissue of the variety 'SMNHPH' was deposited under NCMA Accession number 202303015.

5. A hydrangea plant produced by cultivating the selected spontaneous mutation plant or plant part of claim 4, wherein said hydrangea plant has all the morphological and physiological characteristics of the hydrangea plant of variety 'SMNHPH'.

6. A hydrangea plant produced by cultivating said mutated plant or plant part of claim 4.

7. The method of claim 4, wherein the mutation is introduced using a method selected from the group consisting of: temperature, long-term seed storage, tissue culture conditions, ionizing radiation, chemical mutagens, target induced local lesions in genomes, zinc finger nuclease mediated mutagenesis, CRISPR/Cas9, meganucleases, and gene editing.

8. The method of claim 4, wherein the transgene confers resistance to a herbicide, insects, or disease.

9. A method of producing an F1 seed or embryo, wherein the method comprises crossing a hydrangea plant of variety 'SMNHPH' with a second plant and harvesting the resultant F1 seed or embryo,
   wherein a representative sample of plant tissue of the variety 'SMNHPH' was deposited under NCMA Accession number 202303015.

10. The method of claim 9, wherein the second plant includes another plant of variety 'SMNHPH'.

11. The method of claim 9, wherein the second plant is a plant of a different variety from the variety 'SMNHPH'.

12. A method of producing an F1 seed or an F1 embryo, the method comprising:
   providing a hydrangea plant having one or more physiological and morphological characteristics of a hydrangea plant of variety 'SMNHPH', wherein a representative sample of plant tissue of the variety 'SMNHPH' was deposited under NCMA Accession number 202303015; and
   crossing the hydrangea plant with a second plant and harvesting the resultant F1 seed or embryo, wherein the one or more physiological and morphological characteristics of the hydrangea plant include at least one of orange fall color, a flower panicle density score greater than 85, and flowers that age to a rich, deep pink.

13. The method of claim 12 wherein the one or more physiological and morphological characteristics of the hydrangea plant include a flower panicle density that is greater than 90.

14. A hydrangea plant variety comprising:
   one or more physiological and morphological characteristics of a hydrangea plant of variety 'SMNHPH', wherein a representative sample of plant tissue of the variety 'SMNHPH' was deposited under NCMA Accession number 202303015, wherein the one or more physiological and morphological characteristics of the hydrangea plant include at least one of orange fall color, a flower panicle density score greater than 85, and flowers that age to a rich, deep pink.

15. The hydrangea plant variety of claim 14 wherein the one or more physiological and morphological characteristics of the hydrangea plant include a flower panicle density that is greater than 90.

16. The tissue or cell culture of claim 2, comprising tissues or cells from the hydrangea plant of variety 'SMNHPH selected from the group consisting of leaves, somatic embryos, cotyledons, ovules, protoplasts, callus, petiole, hypocotyl, meristematic cells, roots, root tips, pistils, anther walls, flower petals and stems.

* * * * *

UNITED STATES PATENT AND TRADEMARK OFFICE
CERTIFICATE OF CORRECTION

PATENT NO. : 11,944,063 B2
APPLICATION NO. : 17/354259
DATED : April 2, 2024
INVENTOR(S) : Megan Mathey It is certified that error appears in the above-identified patent and that said Letters Patent is hereby corrected as shown below:

In the Claims

Column 24, Claim 16, Line 67:
"'SMNHPH selected from the group consisting of leaves,"
Should be:
– 'SMNHPH' selected from the group consisting of leaves, –

Signed and Sealed this
Seventh Day of May, 2024

Katherine Kelly Vidal
*Director of the United States Patent and Trademark Office*